US012030256B2

(12) United States Patent
Bhargava et al.

(10) Patent No.: US 12,030,256 B2
(45) Date of Patent: Jul. 9, 2024

(54) COATED TUBULAR CONSTRUCT FOR BIOLOGICAL AND INDUSTRIAL APPLICATIONS AND METHOD OF MAKING A TUBULAR CONSTRUCT

(71) Applicant: THE BOARD OF TRUSTEES OF THE UNIVERSITY OF ILLINOIS, Urbana, IL (US)

(72) Inventors: Rohit Bhargava, Urbana, IL (US); Lin Chen, Urbana, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

(21) Appl. No.: 17/672,924

(22) Filed: Feb. 16, 2022

(65) Prior Publication Data

US 2022/0266534 A1    Aug. 25, 2022

Related U.S. Application Data

(60) Provisional application No. 63/151,502, filed on Feb. 19, 2021.

(51) Int. Cl.
*B29C 64/40* (2017.01)
*A61L 27/16* (2006.01)
(Continued)

(52) U.S. Cl.
CPC .............. *B29C 64/40* (2017.08); *A61L 27/16* (2013.01); *B29C 64/118* (2017.08);
(Continued)

(58) Field of Classification Search
None
See application file for complete search history.

(56) References Cited

U.S. PATENT DOCUMENTS 9,222,932 B2  12/2015  Shepherd et al.
9,851,706 B2  12/2017  Koc et al.
(Continued)

FOREIGN PATENT DOCUMENTS

CA    2803553 A1 * 12/2011
GB    2508018 A  *  5/2014
JP    3748881 B2 *  2/2006

OTHER PUBLICATIONS

Ouyang et al, "Facile Biofabrication of Heterogeneous Multilayer Tubular Hydrogels by Fast Diffusion-Induced Gelation," ACS Appl. Mater. Interfaces, 10 (2018), pp. 12424-12430.
(Continued)

*Primary Examiner* — Tae H Yoon
(74) *Attorney, Agent, or Firm* — Crowell & Moring LLP (57) ABSTRACT

A coated tubular construct for biological and industrial applications includes a plurality of channels, where each channel is radially surrounded by a wall comprising a first polymer, and a conformal coating comprising a second polymer is disposed on an outer and/or an inner surface of each wall. A method of producing a tubular construct includes 3D printing a template structure comprising a sacrificial material and a photoinitiator, and immersing the template structure in a first prepolymer solution comprising a first prepolymer and a co-initiator. During the immersion, the template structure is exposed to light, and the first prepolymer undergoes radical polymerization to conformally coat the template structure with the first polymer, forming a coated template. The sacrificial material is removed from the coated template, and a tubular construct comprising the first polymer is formed.

17 Claims, 7 Drawing Sheets

(51) Int. Cl.
| | |
|---|---|
| B29C 64/118 | (2017.01) |
| B29C 64/209 | (2017.01) |
| B33Y 40/20 | (2020.01) |
| B33Y 70/10 | (2020.01) |
| B33Y 80/00 | (2015.01) |
| C08F 2/50 | (2006.01) |
| C08F 22/10 | (2006.01) |
| B29K 105/00 | (2006.01) |
| B29L 31/18 | (2006.01) |
| B33Y 10/00 | (2015.01) |

(52) U.S. Cl.
CPC ............ *B29C 64/209* (2017.08); *B33Y 40/20* (2020.01); *B33Y 70/10* (2020.01); *B33Y 80/00* (2014.12); *C08F 2/50* (2013.01); *C08F 22/1006* (2020.02); *B29K 2105/0002* (2013.01); *B29K 2995/0059* (2013.01); *B29L 2031/18* (2013.01); *B33Y 10/00* (2014.12)

(56) References Cited

U.S. PATENT DOCUMENTS

| | | | |
|---|---|---|---|
| 10,174,276 | B2 | 1/2019 | Murphy et al. |
| 10,702,630 | B2 | 7/2020 | Lewis et al. |
| 10,933,579 | B2 | 3/2021 | Matheu |
| 2011/0270412 | A1* | 11/2011 | Bellan ..................... A61L 27/56 623/23.72 |
| 2020/0164109 | A1 | 5/2020 | Kroll et al. |

OTHER PUBLICATIONS

Chan et al. "Three-dimensional Photopatterning of Hydrogels Using Stereolithography for Long-Term Cell Encapsulation," Lab Chip, 10, (2010), pp. 2062-2070.

Correia et al., "Minimalist Tissue Engineering Approaches Using Low Material-Based Bioengineered Systems," Advanced Healthcare Materials, 10, 2002110, (2021), pp. 1-18.

Gelber et al., "Model-Guided Design and Characterization of a High-Precision 3D Printing Process for Carbohydrate Glass," Additive Manufacturing, 22, (2018), pp. 38-50.

Grigoryan et al., "Multivascular Networks and Functional Intravascular Topologies within Biocompatible Hydrogels," Science, 364, (2019), pp. 458-464.

Gryka et al., "Controlled Dissolution of Freeform 3D Printed Carbohydrate Glass Scaffolds in Hydrogels Using a Hydrophobic Spray Coating," Additive Manufacturing, 26, (2019), pp. 193-201.

Kadry et al., "Digital Light Processing (DLP) 3D-Printing Technology and Photoreactive Polymers in Fabrication of Modified-Release Tablets," Eur. J. Pharmaceutical Sciences, 135, (2019) pp. 60-67.

Kinstlinger et al., "3D-Printed Fluidic Networks as Vasculature for Engineered Tissue," Lab on a Chip, 16, 2025 (2016), pp. 1-19.

Kizilel et al., "Photopolymerization of Poly(ethylene glycol) Diacrylate on Eosin-functionalized Surfaces," Langmuir, 20, (2004), pp. 8652-8658.

Kolesky et al., "Three-dimensional bioprinting of thick vascularized tissues," Proc. Natl. Acad. Sci., 113, 12 (2016), pp. 3179-3184.

Kolesky, D. B. et al. "3D Bioprinting of Vascularized, Heterogeneous Cell-Laden Tissue Constructs," Advanced Materials, 26, (2014), pp. 3124-3130.

Ladoux et al., "Front-Rear Polarization by Mechanical Cues: From Single Cells to Tissues," Trends Cell Biology 26, 6 (2016), pp. 420-433.

Lee et al., "Guiding Lights: Tissue Bioprinting Using Photoactivated Materials," Chemical Review, 120 (2020), pp. 10950-11027.

Levato et al., From Shape to Function: The Next Step in Bioprinting. Advanced Materials, 1906423, (2020), pp. 1-36.

Lin et al., "Recent Progress in Stem Cell Differentiation Directed by Material and Mechanical Cues," Biomedical Materials 11, 014109 (2016), pp. 1-23.

Liu et al., "Coaxial Extrusion Bioprinting of 3D Microfibrous Constructs with Cell-Favorable Gelatin Methacryloyl Microenvironments," Biofabrication 10, 024102 (2018) pp. 1-11.

Novosel et al., "Vascularization is the Key Challenge in Tissue Engineering," Advanced Drug Delivery Reviews, 63, (2011), pp. 300-311.

Peter et al., "An alternative Technique for Patterning Cells on Poly(ethylene glycol) Diacrylate Hydrogels," The Royal Society of Chemistry Adv. 6, (2016), pp. 40878-40885.

Skylar-Scott et al., "Biomanufacturing of Organ-Specific Tissues with High Cellular Density and Embedded Vascular Channels," Science Advances, 5, eaaw2459 (2019), pp. 1-14.

Wang et al., "Visible Light Photoinitiation of Cell-Adhesive Gelatin Methacryloyl Hydrogels for Stereolithography 3D Bioprinting," ACS Applied Materials and Interfaces 10, (2018), pp. 26859-26869.

Zhu et al., "Gelatin Methacryloyl and its Hydrogels with an Exceptional Degree of Controllability and Batch-to-Batch Consistency," Scientific Reports 9, 6863 (2019), pp. 1-13.

\* cited by examiner

COATED TUBULAR CONSTRUCT FOR BIOLOGICAL AND INDUSTRIAL APPLICATIONS AND METHOD OF MAKING A TUBULAR CONSTRUCT

RELATED APPLICATION

The present patent document claims the benefit of priority under 35 U.S.C. 119(e) to U.S. Provisional Patent Application No. 63/151,502, which was filed on Feb. 19, 2021, and is hereby incorporated by reference in its entirety.

TECHNICAL FIELD

The present disclosure is related generally to polymerization, and more specifically to surface-initiated photopolymerization for fabricating functional tubular constructs.

BACKGROUND

Three-dimensional (3D) printing shows promise as a one-step process for fabricating architectures that resemble living tissues. The technology may be useful in solid organ fabrication, regenerative medicine, and disease models. Highly branched microchannels may play a critical role in transporting fluids and oxygen, facilitating 3D tissue constructs with high cellular density. The ability to fabricate biomimetic vascular networks in vitro is therefore crucial. Several bioprinting techniques, including extrusion-based, stereolithography (SLA), and selective laser sintering (SLS) approaches, have been adopted in an effort to manufacture channel geometries within biocompatible hydrogels. However, scalability and nature-mimicking complexity are often difficult to achieve due to the soft nature of printing materials. Techniques that utilize bioinks to encapsulate viable cells during the printing process generally require well-defined print conditions and a low extrusion pressure to sustain cell viability. Further, these techniques may expose cells to nonphysiological conditions, which may cause unexpected behaviors and damage, while further limiting the biomedical applications. It would be beneficial to develop better methods of preparing microchannel structures that are suited for use in biological and other applications.

BRIEF SUMMARY

A coated tubular construct for biological and industrial applications includes a plurality of channels, where each channel is radially surrounded by a wall comprising a first polymer, and a conformal coating comprising a second polymer is disposed on an outer and/or an inner surface of each wall.

A method of producing a tubular construct includes 3D printing a template structure comprising a sacrificial material and a photoinitiator, and immersing the template structure in a first prepolymer solution comprising a first prepolymer and a co-initiator. During the immersion, the template structure is exposed to light, and the first prepolymer undergoes radical polymerization to conformally coat the template structure with the first polymer, forming a coated template. The sacrificial material is removed from the coated template, and a tubular construct comprising the first polymer is formed.

BRIEF DESCRIPTION OF THE DRAWINGS

FIGS. 8A-8C show examples of printed template structures (left) and the associated tubular constructs after surface-initiated photopolymerization and sacrificial material removal (right) for three different geometries.

DETAILED DESCRIPTION

A new method of producing a tubular construct or a coated tubular construct that may have applications ranging from tissue engineering to industrial heat transfer is described in this disclosure. The method is summarized first in reference to the flow chart of FIG. 1, and then described in greater detail in reference to the schematics of FIGS. 2A-2E.

Figure 1:
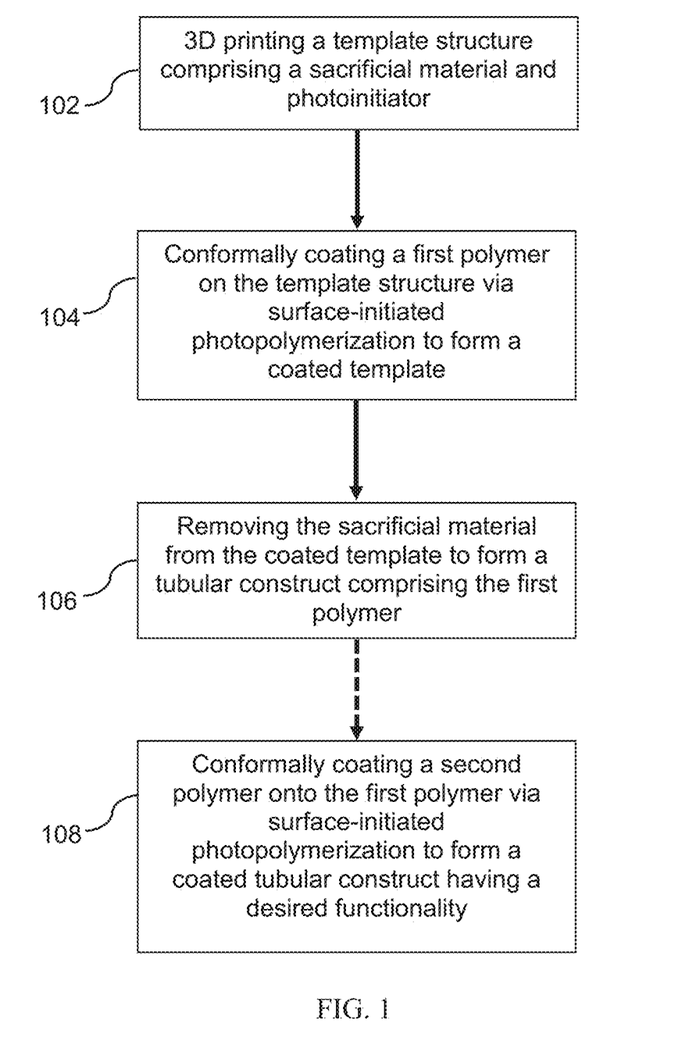
FIG. 1 is a simple flow chart of an exemplary method to form a coated tubular construct having a desired functionality.

Referring first to FIG. 1, the method broadly includes 3D printing 102 a template structure comprising a sacrificial material and photoinitiator, and then conformally coating 104 a first polymer onto the template structure via a first surface-initiated photopolymerization process. After conformal coating, the sacrificial material is removed 106, leaving a tubular (hollow) construct comprising the first polymer. For some applications, the method may further include conformally coating 108 a second polymer onto the first polymer via a second surface-initiated photopolymerization process, thereby forming a coated tubular construct, which may have a desired functionality based on the choice of the second polymer. This optional second conformal coating process may take place before or after removal of the sacrificial material.

Referring now to FIGS. 2A-2E, the method is described in greater detail. The schematics on the left-hand side of each figure provide a perspective view, and the schematics on the right-hand side provide a cross-sectional view of what is illustrated on the left-hand side.

Figure 2A:
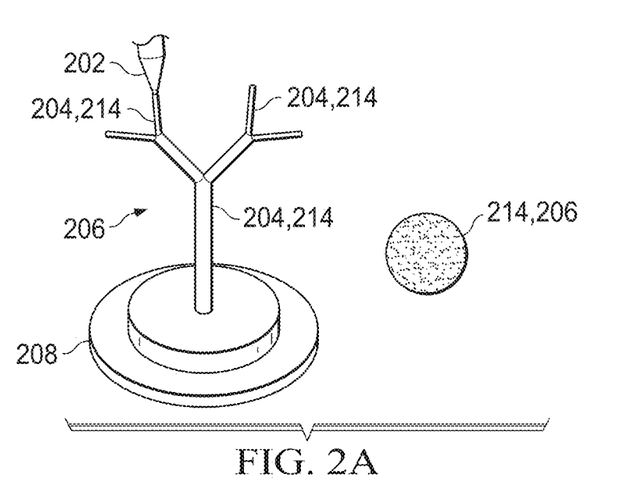
FIGS. 2A-2E are schematic illustrations of the exemplary method of FIG. 1 applied to form a coated tubular construct having a hollow branched geometry.

In FIG. 2A, a filament 204 comprising a sacrificial material and a photoinitiator is extruded 102 through a nozzle 202 moving relative to a substrate 208. One or more of the filaments 204 are deposited on the substrate 208 in a two- or three-dimensional pattern determined by a print path of the nozzle 202, and a template structure 206 comprising the sacrificial material and the photoinitiator is formed or "printed." The template structure 206 may have any desired geometry, such as a branched geometry (as shown), a mesh geometry, a lattice geometry, a cellular geometry, a solid geometry, or any 3D geometry that may be prepared based on the two- or three-dimensional pattern of deposited filament(s) 204. In this example, each branch 214 of the template structure 206 is defined by one or more of the filaments 204. The term "branch" may be generally understood to refer to an extension from an initiation or connection point within the template structure 206; e.g., for a template structure having a mesh geometry, the term branch may refer to extensions between nodes of the mesh. Preferably, the template structure 206 has a sufficient stiffness and/or thickness to be free-standing, as illustrated in FIG. 2A.

The sacrificial material selected for 3D printing may comprise a carbohydrate glass or another material that can be softened or melted at relatively low temperatures for printing and which rapidly stiffens or solidifies after extrusion through the nozzle. It is also preferred that the sacrificial material can be dissolved in a solvent (e.g., water) or otherwise removed after the template structure is printed and conformally coated with the first polymer. In one example, the sacrificial material comprises isomalt ($C_{12}H_{24}O_{11}$). Preferably, the photoinitiator employed for 3D printing is miscible in the sacrificial material to promote even distribution throughout the extruded filament and good printability. In some examples, it is preferred that the photoinitiator is thermally stable up to about 150° C., and/or can further withstand vacuum pressure during a pre-print dehydration process, where water may be removed from the sacrificial material. A suitable photoinitiator may comprise a dye molecule, such as Eosin Y (EY) or EY disodium salt. The photoinitiator may be incorporated in the sacrificial material at a concentration in a range from about 0.5 wt. % to about 3 wt. %. This range is understood to be typical, but the concentration of the photoinitiator is not limited to this range. Additional details about the 3D printing process to prepare the template structure 206 are provided below.

Figure 2B:
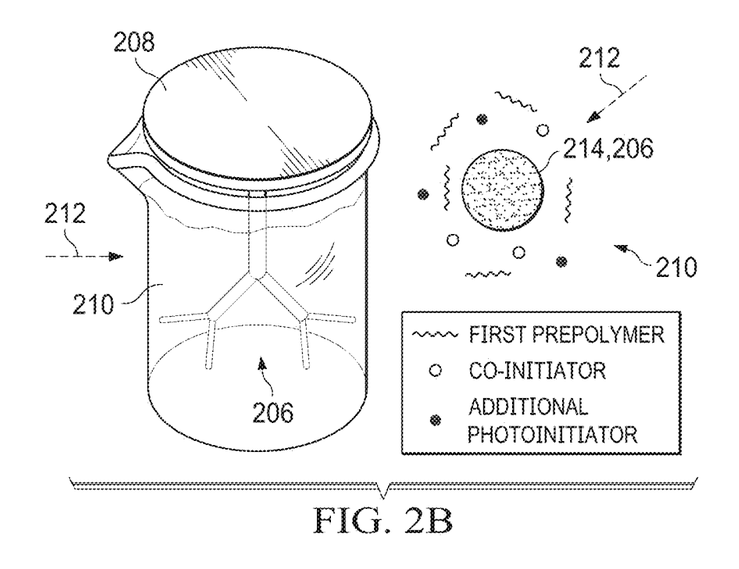

Referring now to FIG. 2B, after printing, the template structure 206 is immersed in a first prepolymer solution 210 comprising a first prepolymer and a co-initiator. The first prepolymer solution 210 may be anhydrous in examples where the sacrificial material is water soluble. The first prepolymer may be an uncured or uncrosslinked precursor of a desired polymer ("first polymer") to be formed during photopolymerization. For example, the first prepolymer may comprise uncrosslinked poly(ethylene) glycol diacrylate (PEGDA), uncrosslinked polyacrylic acid, and/or uncrosslinked polyacrylamide. The first prepolymer solution may contain a solvent capable of dissolving the first prepolymer, such as, in some examples, a mixture of acrylamide (AAm)/choline chloride ($ChCl_2$) (2:1) (mol/mol), and/or a mixture of ethylene glycol (EG)/choline chloride ($ChCl_2$) (2:1). Any monomer having acrylate functional groups be employed as the first prepolymer if incorporated in a suitable solvent. Generally speaking, the first prepolymer may comprise any polymerizable material. The co-initiator may be selected to work in conjunction with the photoinitiator present in the template structure 206 during photopolymerization. In one example, the co-initiator may comprise a tertiary amine such as triethanoloamine (TEOA or TEA) or methyldiethanolamine (MDEA). Typically, the co-initiator is included in the prepolymer solution at a concentration in a range from about 50 mM to about 225 mM, but the concentration is not limited to this range. In some examples, 1-vinyl-2-pyrrolidinone (VP) may be included in the first prepolymer solution 110 to increase the mobility of the polymer chains. The presence of the optional additional photoinitiator shown in FIG. 2B is explained below.

Figure 2C:
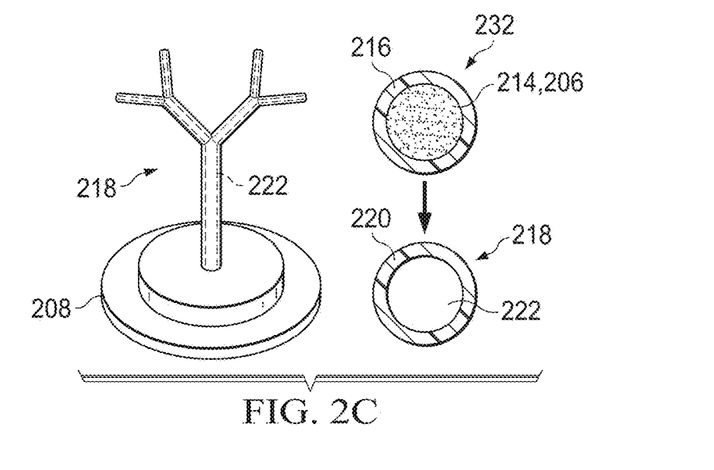

While immersed, the template structure 206 is exposed to light 212 to excite the photoinitiator and the co-initiator, which generate radicals. The light 212 has a wavelength which may depend on the choice of photoinitiator and/or co-initiator. In one example, the light may be green light, and the light may have a wavelength in the range from about 510 nm to about 540 nm. As a consequence of the light exposure and radical generation, the first prepolymer undergoes radical polymerization to form the first polymer, which is conformally coated onto the template structure 206. That is, a conformal coating 216 comprising the first polymer is deposited on the branches 214 of the template structure 206, as illustrated in FIG. 2C (top right schematic), thereby forming a coated template 232.

After conformal coating of the first polymer, the underlying sacrificial material may be removed, leaving a tubular construct 218 comprising the first polymer (bottom right and left schematics). In effect, the template structure 206 is removed, and a tubular construct 218 having walls 220 made of the first polymer is formed. Removal of the sacrificial material may entail rinsing or washing the coated template 232 in water or another liquid in which the sacrificial material is soluble, such that the sacrificial material is flushed from the structure 232, leaving the tubular construct 218.

It is noted that the term "tubular construct" is not limited to a constant diameter geometry but may refer generally to any hollow geometry. For example, consistent with the geometry of the template structure 206 as described above, the tubular construct 218 may have a hollow branched geometry (as illustrated), a hollow mesh geometry, a hollow lattice geometry, a hollow cellular geometry, or another hollow 3D geometry.

Each wall 220 of the tubular construct 218 radially surrounds a channel 222 having a size and orientation determined by the filament(s) 204 deposited during 3D printing. Typically, each filament 204 extruded through the nozzle 202 has a diameter in a range from 10 microns to 1,000 microns, but the diameter is not limited to these sizes. The tubular construct 218 may have a multichannel structure including a plurality of the channels 222. In some examples, the channels 222 may be interconnected to form a network, such as the branched network shown in FIG. 2C. The channel(s) 222 may be configured for transport of biological, industrial or other fluids, such as blood, water, aqueous solutions and/or organic liquids. The walls 220 of the tubular construct 218 may have a thickness determined by the conformal coating of the first polymer, which in turn may be controlled by the duration of the photopolymerization (e.g., time of immersion in the first prepolymer solution and/or time of exposure to light). The walls 220 of the tubular construct 218 may be porous; that is, the walls 220 may contain pores, as discussed in the examples below. Advantageously, inner surfaces of the walls 220 may be smooth.

As indicated above, in an optional step of the method, a second polymer may be conformally coated onto the first polymer, that is, onto the walls 220 of the tubular construct 218, in a second surface-initiated photopolymerization step. The result may be a coated tubular construct having a desired functionality, e.g., enhanced cell adhesion for biomedical applications, or increased thermal conductivity for heat transfer applications, where the second polymer may be selected to provide the desired functionality.

Figure 2D:
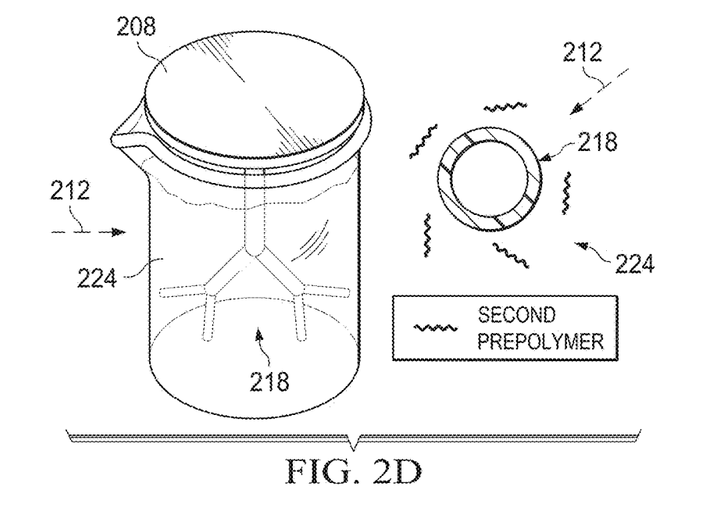

Referring now to FIG. 2D, the second surface-initiated photopolymerization step may entail immersion of the tubular construct 218 in a second prepolymer solution 224 comprising a second prepolymer, along with exposure to light 212 of a suitable wavelength. To promote photopolymerization of the second polymer, it may be beneficial for the first prepolymer solution 210 to include an additional photoinitiator, as illustrated in FIG. 2B, which is selected to facilitate radical polymerization of the second prepolymer. The additional photoinitiator may be included in the first prepolymer solution 210 at a concentration in a range from about 1 wt. % to about 5 wt. %. This range is understood to be typical, but the concentration of the additional photoinitiator is not limited to this range. At the time of the second photopolymerization step, the additional photoinitiator may be understood to be present in the walls 220 of the tubular construct 218. A suitable additional photoinitiator may be 2-hydroxy-4'-(2-hydroxyethoxy)-2-methylpropiophenone (Irgacure 2959). Additional details of the second photopolymerization process are provided below.

The resulting coated tubular construct 226 (see FIG. 2E) may have a multi-layer or multi-wall structure 230 that includes the walls 220 comprising the first polymer and a conformal coating 228 of the second polymer on the walls 220. The second polymer may be conformally coated onto outer and/or inner surfaces of the walls 220 of the tubular construct 218. In other words, the conformal coating 228 comprising the second polymer may be formed on the outer and/or inner surfaces of the walls 220. Accordingly, the coated tubular construct 226 may be described as a dual-wall tubular construct or as a triple-wall tubular construct. The conformal coating 228 comprising the second polymer may be porous; that is, the conformal coating may include pores. For some applications, the method may further include, after forming the coated tubular construct 226, culturing cells on the second polymer, as described in the examples below. Consistent with the geometry of the underlying tubular construct 218, the coated tubular construct 226 may include multiple channels 222 and thus may be described as a coated multichannel structure.

Returning to FIG. 2D and the description of the second surface-initiated photopolymerization step to form the coated tubular construct 226, it is noted that the conformal coating of the second polymer on the first polymer may take place before or after removal of the sacrificial material.

Figure 2E:
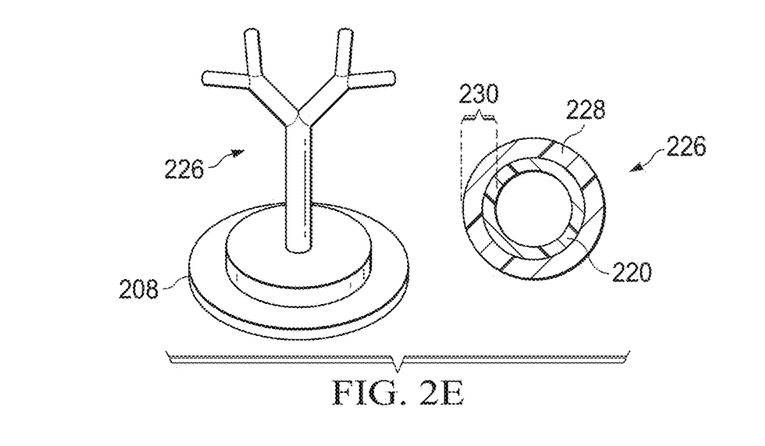

In examples where the second polymer is formed after the sacrificial material is removed, the method may entail immersing the tubular construct 218 into a second prepolymer solution 224 comprising a second prepolymer, as described above and as shown in FIG. 2D. In one example, the second prepolymer may comprise an uncrosslinked hydrogel, such as uncrosslinked gelatin-methacryloyl (GelMA), and the second polymer may comprise a hydrogel such as GelMA after crosslinking. Generally speaking, any photocurable prepolymer may be employed, such as methacrylated collagen, methacrylated hyaluronic acid, methacrylated alginate, and/or PEGDA. The second prepolymer solution may include water or another solvent capable of dissolving the second prepolymer. During the immersion, the tubular construct 218 may be exposed to light 212, such as ultraviolet light (e.g., having a wavelength in a range from about 325 nm to about 395 nm), whereby the additional photoinitiator is excited, radicals are generated, and the second polymer forms via radical polymerization. The light 212 may have a wavelength determined by the additional photoinitiator. Consequently, the second polymer may be conformally coated onto the first polymer, and the coated tubular construct 226 may be formed, as illustrated in FIG. 2E. A conformal coating 228 of the second polymer may be formed on the outer and/or inner surfaces of the walls 220 of the tubular construct 218, although the schematic shows the conformal coating 228 on the outer surface of the wall 220 only. With penetration of light 112 into the channels 220 of the tubular construct 218, conformal coating of the second polymer on the inner surface of the wall 220 may be achieved.

Alternatively, in examples where the second polymer is formed before the sacrificial material is removed, the coated template 232 may be immersed in the second prepolymer solution 224 comprising the second prepolymer. During the immersion, the coated template 232 may be exposed to light 212, e.g., ultraviolet light, such that the additional photoinitiator is excited, radicals are generated, and the second polymer forms via radical polymerization. The light 212 may have a wavelength determined by the additional photoinitiator; in some examples, the wavelength may lie in a range from about 325 nm to about 395 nm. As photopolymerization occurs, a conformal coating 228 of the second polymer may form on the conformal coating 216 of the first polymer, and then the sacrificial material may be removed (e.g., as described above), leaving the coated tubular construct 226. In this example, the second polymer may be coated onto outer surfaces of the walls 220 of the tubular construct 218.

If desired, one or more additional conformal coatings comprising one or more additional polymers may be applied to the coated tubular construct 226 by carrying out further surface-initiated polymerization steps, each with a suitable prepolymer solution and wavelength of light exposure.

The first polymer may be any natural or synthetic polymer that may formed by curing or crosslinking upon exposure to light of a predetermined wavelength or range of wavelengths (photopolymerization). For example, the first polymer may comprise poly(ethylene) glycol diacrylate (PEGDA), polyacrylic acid, and/or polyacrylamide. After crosslinking, the first polymer preferably exhibits a sufficient stiffness to form a freestanding tubular construct. Similarly, the second polymer may be any polymer that may be formed by curing or crosslinking upon exposure to light of a predetermined wavelength or range of wavelengths. In some cases, the second polymer may be selected to provide a desired functionality. In experiments described below, the second polymer comprises a hydrogel, more specifically, gelatin-methacryloyl (GelMA), to provide enhanced cell adhesion, e.g., when the coated tubular construct forms part or all of a tissue or organ construct. In other examples, the second polymer may be selected to provide other functionality, such as thermal conductivity, e.g., when the coated tubular construct forms part or all of a heat exchanger. The one or more additional polymers that may be applied in subsequent surface-initiated polymerization steps may be the same as or different from the first and second polymers. Generally speaking, the one or more additional polymers may comprise any natural or synthetic polymer(s) that may be formed by curing or crosslinking upon exposure to light of a predetermined wavelength or range of wavelengths.

A total wall thickness of the coated tubular construct 226 may refer to the thickness of the walls 220 comprising the first polymer in addition to the thickness added by the conformal coating 228 of the second polymer onto the inner and/or outer surfaces of the walls 220. Accordingly, the total wall thickness may be determined by the first and second conformal coating steps, which maybe controlled by the time of immersion in the first and second prepolymer solutions and/or the time of exposure to light in each photopolymerization step. Typically, the total wall thickness may lie in a range from about 50 microns to about 500 microns, or from about 70 microns to about 150 microns, but is not limited to these values. The total wall thickness may span the micrometer to the millimeter range.

Each channel 222 may have a diameter in a range from about 10 microns to about 5,000 microns, from about 50 microns to about 1,000 microns, or more typically from about 100 microns to about 400 microns. Given the 3D printing process employed to form the template structure 206, the diameter of each channel 222 may be largely or entirely determined by the diameter of each filament 204, as indicated above. Thus, by controlling the 3D printing process, the diameter of the channels 222 may be made as large or as small as desired. In addition, by using different-size nozzles for 3D printing, varying the printing parameters, and/or layering the deposited filament(s) 204, it may be possible to produce tubular constructs 218 (and thus coated tubular constructs 226) having channels 222 of different diameters and/or channels 222 of variable (or constant) diameters along the respective lengths.

The 3D printing process employed to prepare the template structure 206 is now described in further detail. As indicated above, in one example, the sacrificial material comprises isomalt ($C_{12}H_{24}O_{11}$), and the photoinitiator may comprise a dye molecule, such as Eosin Y (EY) or EY disodium salt. Typically, photoexcitation of EY allows controlled single-electron transfer to other organic substrates to generate reaction initiators. An advantage of using an EY polymerization scheme is a broad absorption profile with a peak (~524 nm) at the shorter wavelength end of the visible part of the spectrum. This makes this photoinitiator highly compatible with commonly available and economical light sources. Additionally, the use of visible excitation provides lower cytotoxicity compared to UV excitation of the photoinitiator, which may be important for biomedical applications.

Prior to printing, the sacrificial material may be melted and mixed with the photoinitiator and, in some examples (such as when isomalt is employed), dehydrated to remove excess water, thereby forming a precursor material for printing. The precursor material comprising the sacrificial material and the photoinitiator may be supplied to the nozzle through a printhead which may be electronically connected to a motion controller. As described above, during printing, one or more filaments comprising the sacrificial material and the photoinitiator are deposited on a substrate in a 2D or 3D pattern to form (or "print") the template structure. During the extrusion, the nozzle may be heated to a temperature above a softening and/or melting temperature of the sacrificial material, such as greater than 100° C., or greater than 125° C., to promote flow through the nozzle. After being extruded through the nozzle, the one or more filaments comprising the sacrificial material and the photoinitiator may stiffen and/or solidify to form a template structure that preferably is sufficiently rigid to be free-standing on the substrate. Each filament extruded through the nozzle may have a diameter in a range from about 10 microns to 1,000 microns, and/or in the range from about 100 microns to about 400 microns. The motion of the nozzle relative to the substrate may be carried out by translation of the nozzle only, by translation of the substrate only, or by translation of both the nozzle and the substrate.

In addition to the above-described method, a coated tubular construct for biological or industrial applications is described. Referring to FIG. 2E, the coated tubular construct 226 includes a plurality of channels 222, where each channel is radially surrounded by a wall 220 comprising a first polymer, and a conformal coating 228 comprising a second polymer is disposed on an outer and/or an inner surface of each wall 220.

Figure 6A:
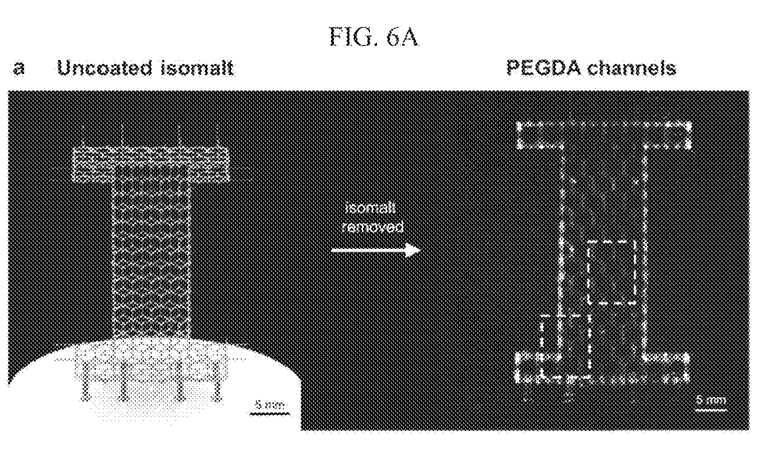
FIG. 6A shows images of a printed template structure (left) and a tubular construct formed after surface-initiated photopolymerization (right).
Figure 6B:
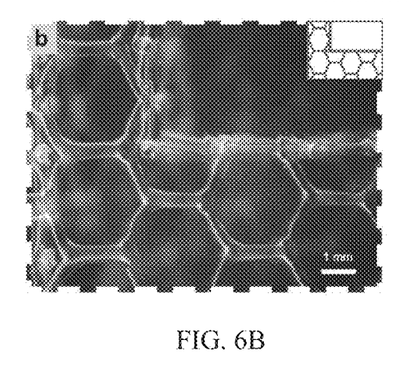
FIGS. 6B and 6C show higher magnification stereo microscope images of parts of the tubular construct of FIG. 6A, as indicated by the dashed boxes.
Figure 6C:
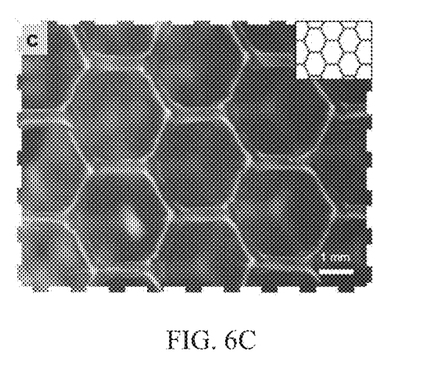

The channels 222 may be interconnected to form a network of channels, as illustrated in FIG. 2C, where the dotted lines show the channels 222 within the tubular construct 218 prior to application of the conformal coating 228 comprising the second polymer. The channels 222 and/or the network of channels may be configured for transport of biological, industrial and/or other fluids, such as blood, water, aqueous solutions and/or organic liquids. The coated tubular construct 226 may have any desired hollow geometry, such as a hollow branched geometry, as illustrated in FIG. 2E, a hollow mesh or lattice geometry, as shown in FIG. 8B, or a hollow cellular geometry, as shown in FIG. 6C. Other 3D hollow geometries that can be fabricated by the method described above are also possible. Each channel 222 may have a diameter in a range from about 10 microns to about 1,000 microns, although the diameter is not limited to this range. The walls 220 and/or the conformal coatings 228 on the walls 220 may be porous; that is, the walls and/or the conformal coatings may include pores. Typical pore sizes may range from 10 μm to about 50 μm.

Each wall 220 may have a nominal thickness in a range from about 30 microns to about 80 microns, which may be determined by the surface-initiated photopolymerization process described above. However, the nominal thickness of each wall 220 is not limited to this exemplary range. Also or alternatively, each wall 220 may have a uniform thickness; that is, the thickness of the wall 220 measured at any point about the circumference of the channel may lie within +/−10% of the nominal thickness, or within +/−5% of the nominal thickness. Similarly, each conformal coating 228 may have a nominal thickness in a range from about 50 microns to about 100 microns, which may be determined by the surface-initiated photopolymerization process described above. It is understood that the nominal thickness of each conformal coating 228 is not limited to this exemplary range. Also or alternatively, each conformal coating 228 may have a uniform thickness; that is, the thickness of the conformal coating measured at any point about the circumference of the channel may lie within +/−10% of the nominal thickness, or within +/−5% of the nominal thickness.

The first polymer may comprise poly(ethylene) glycol diacrylate (PEGDA), polyacrylic acid, and polyacrylamide. The second polymer may comprise a hydrogel, such as GelMA. For biological applications, the coated tubular construct 226 may further include cells adhered to the conformal coating 228 comprising the second polymer. In one example, the coated tubular construct 226 may form part or all of a tissue or organ construct. Alternatively, the conformal coating 228 may be configured to serve another function, such as provide enhanced heat or mass transfer. In such an example, the coated tubular construct 226 may form part or all of a heat exchanger.

Example 1: Fabrication of Tubular Constructs

Figure 3:
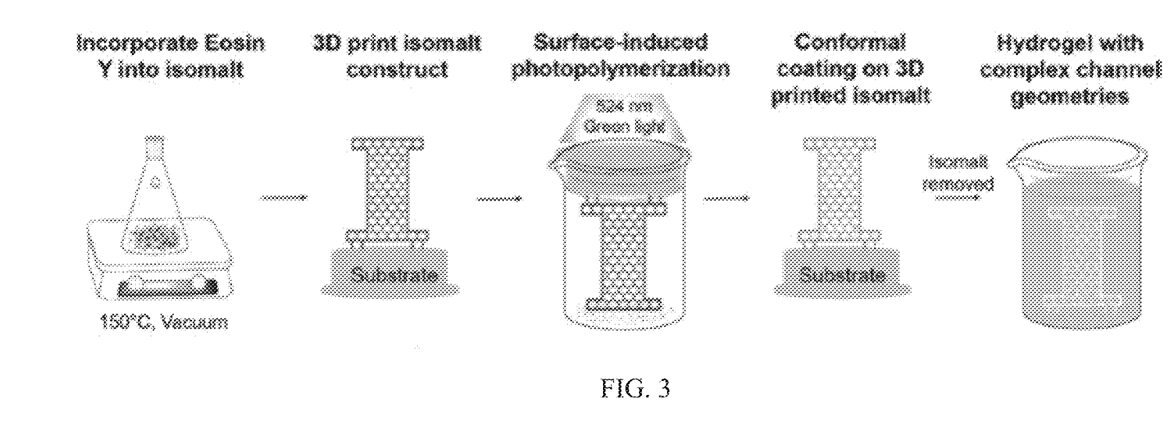
FIG. 3 is schematic illustration of the exemplary method of FIG. 1 applied to form a coated tubular construct having a hollow cellular geometry.

Provided below is a description of an exemplary process in which 3D printing is combined with surface-initiated photopolymerization (SIP) to form a tubular construct. The process is facilitated by appropriate preparation of printing materials (the sacrificial material and the photoinitiator) and controlled photopolymerization. Referring to FIG. 3, a suitable concentration of the photoinitiator (Eosin Y disodium salt (EY) in this example) is mixed with the sacrificial material (isomalt in this example) in a pre-print dehydration process, and then the sacrificial material mixed with the photoinitiator is 3D-printed. The resulting template structure is immersed into a prepolymer solution including uncross-linked PEGDA and a co-initiator (TEA in this example), and exposed to light to excite the EY/TEA radical polymerization system to initiate polymerization. SIP around the template structure is thus achieved, creating a conformal coating comprising the PEGDA localized near the surface. After coating, the sacrificial material (isomalt) is washed and removed with water, leaving a tubular construct with walls comprising the PEGDA.

Materials:

EY (≥90%), PEGDA (average $M_n$=700), TEA (≥99.0%), and 1-vinyl-2-pyrrolidinone (VP) (≥98.0%) were provided. Isomalt (galenIQ 990) was provided. Substrates were 3D printed using a Form 2 SLA printer using a FLGPCL04 clear resin.

Calculation of Solubility Parameters:

High solubility of the photoinitiator (EY) in the sacrificial material (isomalt) is beneficial for reliable fabrication of 3D printed structures. The solubility can be determined by defining each material's solubility parameter. The solubility parameter (δ) of a given material can be calculated from the cohesive energy or from the molar attraction constant (δ=F/V), as described in detail in the priority application, which is incorporated by reference above. The difference in solubility parameters of isomalt with common photoinitiators indicates a range of potential miscibility. The calculations reveal poor miscibility for photoinitiators 2-hydroxy-4'-(2-hydroxyethoxy)-2-methylpropiophenon (Irgacure 2959) and 2,2-dimethoxy-2-phenylacetophenone (DMPA), which was verified experimentally. To select a solubility parameter cutoff for miscibility, water was chosen as a reference. With this criterion, 1-hydroxycyclohexyl phenyl ketone ($δ_t$=36.78 $MPa^{1/2}$) and Eosin Y ($δ_t$=31.92 $MPa^{1/2}$) disodium salt had closer total solubility parameters with isomalt ($δ_t$=39.52 $MPa^{1/2}$), indicating that they could be miscible. Physical characteristics were also considered. Due to its low melting point (45-50° C.), boiling point (175° C.), and flash point (164° C.), 1-hydroxycyclohexyl phenyl ketone may not be compatible with the preprint dehydration process and the hot-melt extrusion process of the isomalt printer. The dye-based, type-two photoinitiator Eosin Y disodium salt was deemed suitable due to its miscibility with isomalt and good thermal stability.

Preprint Material Processing:

To achieve high print quality, it is beneficial to prevent co-crystallization between isomalt and water. Isomalt was dehydrated before being loaded into the freeform 3D printer. This preprint dehydration process intends to also include Eosin Y molecules into isomalt. Isomalt was blended with 0.5% (w/w) Eosin Y and left in a flask under 150° C. and vacuum-pressured for 3 h. After processing, molten isomalt was carefully poured into aluminum molds to form solid cylindrical sticks. Isomalt sticks were stored in flushing oil to avoid moisture in air.

Freeform 3D Printing:

Isomalt constructs were printed using a custom printer with 110 μm and 160 μm nozzles (Subrex). About 10 g of the isomalt stick was loaded into the printer barrel and covered with a layer of flushing oil. The temperature at the printer barrel zone was set to 126° C., and the temperature at the nozzle zone was set to 132° C. The extrusion pressure was set to 100 psi for a 110 μm nozzle and 75 psi for a 160 μm nozzle. Designs were printed at 0.4 mm/s on custom cylindrical substrates fabricated using the Form 2 SLA printer (Formlabs). The printing enclosure was continuously purged with nitrogen to maintain the humidity under 20%. After printing, isomalt constructs were stored under nitrogen. Before coating, isomalt was washed with hexane to remove residual flushing oil.

Surface-Initiated Photopolymerization System:

A prepolymer solution (or "bath") was prepared by mixing a PEGDA prepolymer, TEA, and VP. The final prepolymer solution contained 3% (v/v) TEA and 5% (v/v) VP. To achieve 3D photopolymerization, a custom-made green light box was built by assembling six green LED arrays. Light intensity (41.5 $W/cm^2$) was measured with a FieldMaxII-P laser energy meter (RoHS).

Figure 4:
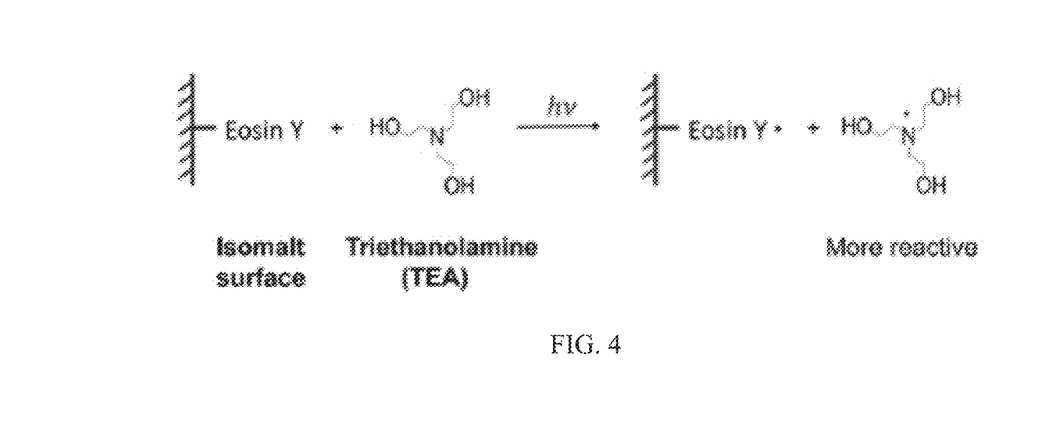
FIG. 4 illustrates activation of an exemplary photoinitiator (Eosin Y) and co-initiator (triethanolamine) by exposure to green light.

Surface-Initiated Photopolymerization:

Upon exposure to green light (524 nm), Eosin Y disodium salt on isomalt surfaces is excited to its triplet state, further accepting electrons from its co-initiator, TEA, which is distributed in the PEGDA prepolymer bath to create two radical initiators, as illustrated in FIG. 4. Though TEA is distributed in the entire bath, it is hypothesized that surface-initiated radicals have a short life span due to rapid polymerization kinetics. This short lifespan limits diffusion of radical species into the bulk prepolymer bath, which is key to obtaining conformal coatings. To test the validity of this approach and ability to obtain uniform coatings, SIP was undertaken around freeform 3D printed constructs, as shown for the example using a 3 mm wide bridge structure with 0.5% EY (w/w). After printing, the bridge construct was immersed into the PEGDA prepolymer bath containing TEA and exposed to green light for 10 min. Sacrificial isomalt was then washed off with water, leaving a free-standing PEGDA tubular construct. ATR-FTIR spectroscopy was used to compare the spectra between bulk PEGDA, surface-polymerized PEGDA, and isomalt with 0.5% Eosin Y disodium salt. Absorption of the carbonyl groups at 1724 $cm^{-1}$ was observed in the spectra of bulk-cured PEGDA gel and SIP-PEGDA. The spectra indicated that polymerization on isomalt substrates was similar to that in bulk PEGDA hydrogel, indicating that surface-polymerized PEGDA was successfully achieved. Differences in polymerization may be useful to estimate important functional characteristics of the surface layer, such as structural rigidity (related to gelation) and potential swelling (related to cross-link density). While sufficient structural fidelity is observed as the structure maintains its shape over time and exhibits robustness in handling, it was of interest to quantify the swelling ability of the scaffold directly. A swelling ratio (SR) was defined in this study by length change because it is difficult to accurately quantify the water content in the channels themselves. The observed SR of PEGDA hydrogels fabricated via SIP (22.92±1.41%) was higher than that of bulk polymerized PEGDA hydrogels (20.99±1.19%) with the same precursor bath and exposure time. This suggests that hydrogels synthesized via SIP have a slightly lower cross-link density and possibly somewhat larger mesh sizes compared to bulk cross-linked PEGDA. Whether this small difference translates into functional differences in use of the materials naturally depends on the application; given the small spectral and functional differences, however, the functionality of SIP-PEGDA can be expected to be close to that of the bulk hydrogel.

Figure 5:
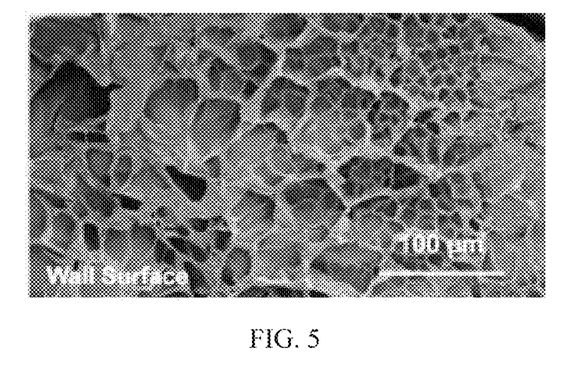
FIG. 5 shows a scanning electron microscope (SEM) image of a wall of a tubular construct comprising poly (ethylene) glycol diacrylate (PEGDA) and having a porous structure.

Characterization of Surface Morphology:

In addition to physical and swelling characteristics, surface characteristics of the cross-linked PEGDA are important for determining biological use. Hence, the surface morphology of the SIP PEGDA tubular construct was characterized. For tissue engineering scaffolds, in particular, both hollow channel geometries and micropores within the channel walls are crucial for mass transfer. To test the morphology in a channel geometry, an interconnected scaffold (10 mm×10 mm×3.5 mm) having a square lattice geometry was printed and coated with PEGDA via SIP. After removal of the sacrificial material (isomalt), the tubular PEGDA structure was lyophilized to retain the porous structures for scanning electron microscopy (SEM). A square-like spacing was maintained within the scaffold, and higher magnifications revealed a porous morphology of the walls of the channels, indicating that polymerization via SIP generates porous structures, as shown in FIG. 5. The pore sizes range from about 10 µm to about 50 µm. These results demonstrate that the above-described method can create porous surface morphologies as well as channel geometries.

Complex Freeform Printed Structures with Surface-Induced Photopolymerization:

This coating method can be expanded to coat complex multichannel structures with smaller diameters. A complex "block I" design, composed of a mesh network of 200-250 µm filaments providing structures at different scales, was printed and then coated, as previously described. After removal of the isomalt support, the PEGDA multichannel structure was able to remain a free-standing construct in water, as shown in FIG. 6A. Optical images, taken under a stereo microscope, show details of the multichannel structure, demonstrating the high fidelity of the approach. Further, a 3D solid shape ("Stanford bunny") was printed layer-by-layer and coated to demonstrate that the method is capable of producing complex hollow structures. The hollow structure was free-standing and retained good fidelity in water. Also, to show perfusion ability of multicellular structures, perfusion through a bifurcated structure was demonstrated. The polymeric walls of the structure remain intact after a long period of time (more than 1 month), showing time-stability in an aqueous environment. The results suggest that this SIP coating system may be a reliable means toward a variety of printed geometries with different angles, such as filaments, curved geometries, perpendicular features, and curvatures.

Example 2: Fabrication of Coated Tubular Construct with Enhanced Cellular Adhesion In this example, the above-described method to form multiple conformal coatings on 3D printed template structures via surface-initiated wavelength-selective photopolymerization is described. By utilizing different adsorption wavelengths, multi-layered polymer coatings were formed around the template structures, providing precise control of both scaffold dissolution and cell adhesion. The printability and coating ability to form scalable scaffolds (from millimeter- to centimeter-scale) with enhanced cellular adhesion on both 2D and 3D structures are demonstrated.

First, a sacrificial material, composed of isomalt and Eosin Y (EY) is 3D printed. Next, the printed template is immersed into a bath of anhydrous PEGDA prepolymer which contains a UV curable photoinitiator—Irgacure 2959. Upon exposure to green light (~525 nm), the EY in the sacrificial template is then excited as a photosensitizer, facilitating a conformal crosslinked polymeric coating around the 3D template structures, yet the Irgacure 2959 remained unactuated. The isomalt sacrificial material was then removed by rinsing with water, leaving PEGDA polymeric tubular constructs with similar structural fidelity as the carbohydrate template.

For isomalt 3D printing, a PEGDA prepolymer solution provides an anhydrous bath for forming protective coatings. However, the anti-fouling and low cell-adhesion property of PEGDA may hamper its application in tissue engineering scaffolds. This challenge may be overcome by directly forming a coating of a second polymer, such as GelMA, which functions as a cell adhesive material, on the PEGDA coating. A wavelength-selective coating system is employed to polymerize a GelMA prepolymer, forming a dual-layer tubular construct. By using the different adsorption wavelengths of Eosin Y and Irgacure 2959, this method enables the formation of different polymer coatings upon sequential exposure to green (~524 nm) and UV (~365 nm) light.

Figure 7:
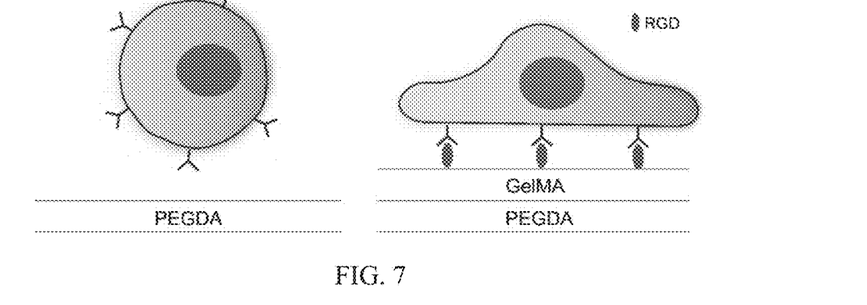
FIG. 7 is a schematic illustrating the enhanced cellular adhesion obtained from a gelatin-methacryloyl (GelMA)-coated tubular construct compared to an uncoated tubular construct comprising PEGDA.

To fabricate 3D printed template structures with photoreactivity, isomalt granules and EY powder are mixed under vacuum pressure and 150° C. The high temperature allows molten isomalt to dissolve EY, and the vacuum pressure facilitates the removal of extra water from the isomalt, which is important for better printability. Next, the 3D printed template structures are immersed into an anhydrous prepolymer solution. The prepolymer solution contains liquid phase PEGDA, Irgacure 2959, triethanolamine (TEOA or TEA), and 1-vinyl-2-pyrrolidinone (VP). Upon exposure to green light, a conformal coating comprising crosslinked PEGDA forms around the isomalt template structure. The crosslinked polymer forms due to the creation of EY and TEOA radicals, resulting in radical polymerization around the 3D printed template structures. The isomalt is removed by immersing the coated template in a water bath. By immersing the structure into a second prepolymer solution, which contains 5% of GelMA prepolymer, and exposing the second prepolymer solution to UV light, Irgacure 2959 is activated, and a second polymer coating is formed. With the second polymer layer, the coated tubular constructs exhibit enhanced cellular adhesion due to the Arg-Gly-Asp (RGD) adhesion motif within the GelMA material, as illustrated in FIG. 7.

Figures 8A, 8C:
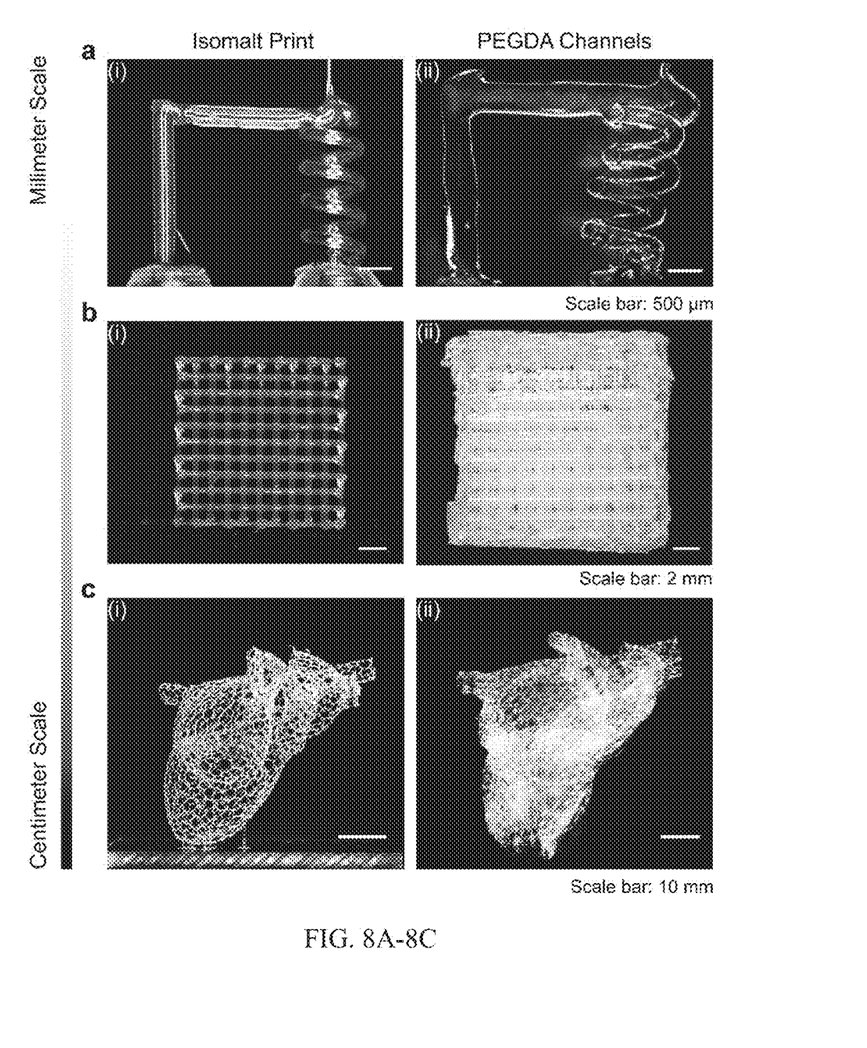

The printability of isomalt and the coating ability of surface-initiated photopolymerization (SIP) is demonstrated in FIGS. 8A-8C, where the template structure is shown on the left (figures labeled (i), and the multichannel structure is shown on the right (figures labeled (ii)). Due to the stiff nature of isomalt, free-standing and multi-scalable template structures may be printed. Fabrication of three template geometries are shown: a simple bridge with helix, a square lattice, and a complex mesh heart. These exemplary printed template structures were composed of filaments with 100-400 µm diameters. Following SIP and removal of isomalt, tubular constructs having good fidelity were obtained that remained free-standing in water. Scalability of the printed template structures spans from millimeter scale to centimeter scale. The multi-scalable capability indicates that SIP can fabricate tubular constructs for a variety of studies. In addition, SIP method creates structures with minimal material, which has the potential to create scaffolds that allow maximal cellular crosstalk or self-arrangements.

Figure 9:
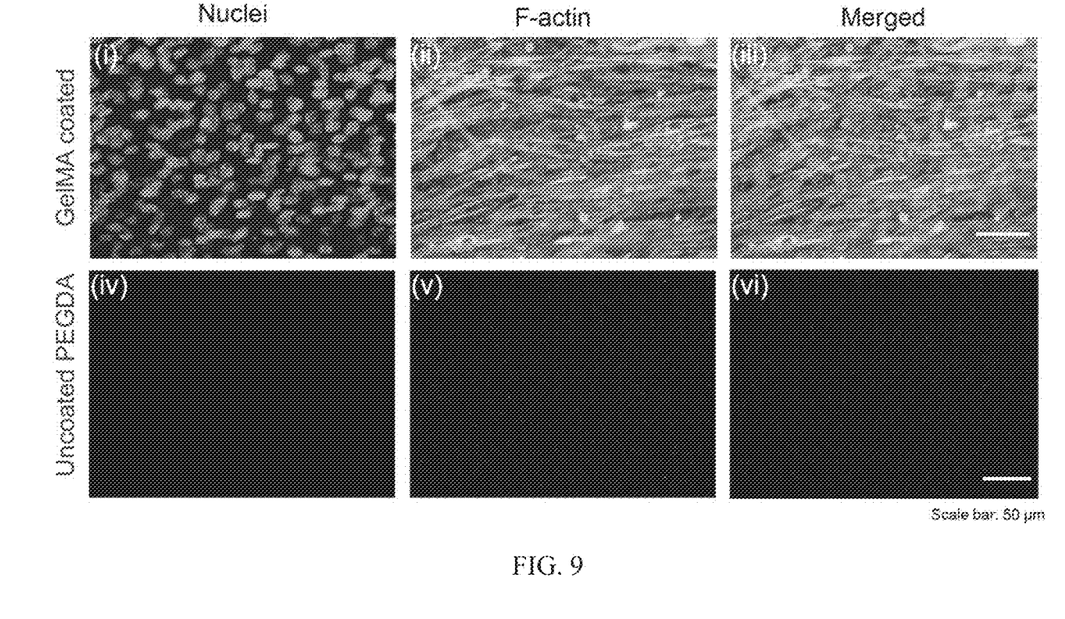
FIG. 9 shows confocal fluorescence images of uncoated PEGDA and GelMA-coated surfaces to compare cell morphology at day five of cell culture experiments.

To validate that enhanced cellular adhesion can be achieved through the dual-photoinitiator system, the adhesion performance of cells on different surfaces was investigated. GelMA-coated PEGDA pellets were fabricated as described above. First, a PEGDA prepolymer that contained both Eosin Y and Irgacure 2959 was polymerized with exposure to green light. The cured PEGDA pellet was then immersed into a 5% GelMA aqueous solution and exposed to UV light, which activated the remaining photoinitiator (Irgacure 2959) and formed the GelMA coating. The coated samples were further washed by water to remove uncured GelMA. The cellular adhesion of uncoated PEGDA and GelMA-coated surfaces was compared. Cell culture was conducted on both surfaces (n=3), followed by live and dead staining and fluorescence imaging. Since day one, the GelMA-coated surface has shown better adhesion compare to PEGDA. From day one to day five, a continuous increase of cell density is observed, suggesting that the GelMA-coated surfaces present low cytotoxicity. For visualization of cell-morphology, confocal fluorescence images of uncoated PEGDA and GelMA-coated surfaces were taken at day five, as shown in FIG. 9. The PEGDA surface demonstrated few live cells, while the GelMA-coated surface presents morphologically correct cardiac myocyte images.

In addition, cell culture conducted on two-layered 3D tubular constructs combined with confocal fluorescence imaging showed that enhanced cellular adhesion can be achieved and further that cells are able to adhere around the entire 3D channel.

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein.

Furthermore, the advantages described above are not necessarily the only advantages of the invention, and it is not necessarily expected that all of the described advantages will be achieved with every embodiment of the invention.

The invention claimed is:

1. A coated tubular construct for biological applications, the coated tubular construct comprising:
   a plurality of channels, each channel being radially surrounded by a wall comprising a first polymer, a conformal coating comprising a second polymer disposed on an outer and/or an inner surface of the wall, and one or more additional conformal coatings on the conformal coating disposed on the outer and/or the inner surface of the wall, the one or more additional conformal coatings comprising one or more additional polymers,
   wherein the first polymer is selected from the group consisting of poly(ethylene) glycol diacrylate (PEGDA), polyacrylic acid, and polyacrylamide, and wherein the coated tubular construct is free-standing.

2. The coated tubular construct of claim 1, wherein the walls and/or the conformal coatings comprise pores.

3. The coated tubular construct of claim 1, wherein each channel has a diameter in a range from about 10 microns to about 5,000 microns.

4. The coated tubular construct of claim 1 having a hollow geometry selected from the group consisting of: a hollow branched geometry, a hollow mesh geometry, a hollow lattice geometry, and a hollow cellular geometry.

5. The coated tubular construct of claim 1, wherein the second polymer comprises a hydrogel.

6. The coated tubular construct of claim 1, further comprising cells adhered to the second polymer.

7. The coated tubular construct of claim 1 forming part or all of a tissue or organ construct.

8. The coated tubular construct of claim 1, wherein the channels are configured for transport of biological fluids.

9. The coated tubular construct of claim 1, wherein the second polymer is configured for cell adhesion.

10. The coated tubular construct of claim 1, wherein the second polymer comprises gelatin-methacryloyl (GelMA).

11. The coated tubular construct of claim 1, wherein the channels are interconnected to form a network.

12. The coated tubular construct of claim 1, wherein the one or more additional polymers comprise one or more natural or synthetic polymers formed by curing or cross-linking upon exposure to light of a predetermined wavelength or range of wavelengths.

13. The coated tubular construct of claim 1, wherein each wall has a uniform thickness and/or each conformal coating has a uniform thickness.

14. The coated tubular construct of claim 1 having a total wall thickness in a range from about 50 microns to about 500 microns.

15. The coated tubular construct of claim 1, wherein the channels have variable diameters along their respective lengths.

16. The coated tubular construct of claim 2, wherein the pores range in size from about 10 μm to about 50 μm.

17. The coated tubular construct of claim 1, wherein the first and second polymers are formed by curing or cross-linking upon exposure to light of a predetermined wavelength or range of wavelengths.

* * * * *